(12) United States Patent
Gaedicke et al.

(10) Patent No.: US 7,582,778 B2
(45) Date of Patent: Sep. 1, 2009

(54) PODOPHYLLOTOXIN

(75) Inventors: Gerhard Gaedicke, Berlin (DE); Holger N. Lode, Berlin (DE); Wolfgang Wrasidlo, LaJolla, CA (US)

(73) Assignee: Universitatsklinikum Charite der Humboldt-Universitat zu (DE)

( * ) Notice: Subject to any disclaimer, the term of this patent is extended or adjusted under 35 U.S.C. 154(b) by 578 days.

(21) Appl. No.: 10/497,521

(22) PCT Filed: Dec. 3, 2002

(86) PCT No.: PCT/EP02/13669

§ 371 (c)(1),
(2), (4) Date: Aug. 11, 2004

(87) PCT Pub. No.: WO03/048166

PCT Pub. Date: Jun. 12, 2003

(65) Prior Publication Data

US 2006/0293254 A1  Dec. 28, 2006

(30) Foreign Application Priority Data

Dec. 3, 2001  (DE)  ................................. 101 60 515

(51) Int. Cl.
*C07D 307/77*  (2006.01)
(52) U.S. Cl. ..................................... 549/298
(58) Field of Classification Search ........................ None
See application file for complete search history.

(56) References Cited

U.S. PATENT DOCUMENTS 5,681,567 A    10/1997  Martinez et al.

FOREIGN PATENT DOCUMENTS

EP    0 320 988 A2    6/1989

OTHER PUBLICATIONS

Daley et al. Journal of Medicinal Chemistry, 1998, 41, 4475-4485.*
Wrasidlo et al. Bioorganic & Medicinal Chemistry Letters, 12 (2002) 557-560.*
W. Wrasidlo et al., "Synthesis, Hydrolytic Activation and Cytotoxicity of Etoposide Prodrugs", Bioorg. Med. Chem. Lett., vol. 12, No. 4, 2002, pp. 557-560.
L. Daley et al., "Synthesis and Antitumor Activity of New Glycosides of Epipododphyllotoxin, Analogues of Etoposide, and NK 611", J. Med. Chem., vol. 41, No. 23, Oct. 17, 1998, pp. 4475-4485.
A. Niethammer et al., "Synthesis and Preclinical Characterization of a Paclitaxel Prodrug with Improved Antitumor Activity and Water Solubility", Bioconjugate Chem., vol. 12, No. 3, Apr. 27, 2001, pp. 414-420.
Nicolaou et al., "Design, synthesis and biological activity of protaxols", Nature, vol. 364, Jul. 29, 1993, pp. 464-466.

* cited by examiner

*Primary Examiner*—D. Margaret Seaman
*Assistant Examiner*—Nizal S Chandrakumar
(74) *Attorney, Agent, or Firm*—Rothwell, Figg, Ernst & Manbeck, p.c.

(57) ABSTRACT

The invention relates to podophyllotoxins, uses thereof and methods of their production.

2 Claims, 6 Drawing Sheets

PODOPHYLLOTOXIN

CROSS REFERENCE TO RELATED APPLICATION

This application is a 35 USC § 371 National Phase Entry Application from PCT/EP02/13669, filed Dec. 3, 2002, and designating the U.S.

Lignans, such as podophyllotoxin and its metabolites/precursors are part of the phenylpropanoid pathway and are widely distributed throughout the plant kingdom. Some of them, in particular podophyllotoxin itself, are known to have anticancer, antifungal and/or antimicrobial properties. Podophyllotoxin was first extracted from may apple (*Podophyllum peltaturm*) and from *Linum* species, such as *Linum album, Linum flavum* and *Linum nodiflorum* as a resin and was used by physicians in the southern parts of the USA in the late $19^{th}$ century for the treatment of genital warts, the latter being associated with some parts of cancer through their etiology by human papillomavirus (HPV). Podophyllotoxin has gained particular interest as the parent molecule of chemotherapeutic drugs such as etoposide, teniposide and etopophos, which are inhibitors of topoisomerase II. At present, the demand for podophyllotoxin outreaches the global supply by far, which has become insufficient due to slow growth and overcollection of the wild plants. In order to compensate for the limited supply of podophyllotoxin attempts have been undertaken to cultivate cells of *Podophyllum peltatum* and *Linum album* which, to some extent have been successful. The semisynthetic derivatives, etoposide and teniposide are widely used important anticancerdrugs, but they have several limitations, such as poor water solubility, metabolic inactivation and the development of drug resistance. To overcome these limitation derivatives of podophyllotoxin have been synthesised in many laboratories (Yin et al., acta pharm. Sinica 1993, 28,758-761, Wang et al., acta chem. Sinica 1992, 50, 698-701, Chang et al., J. med. chem. 1994, 37446-442, Pelter et al., J. nat. prod. 1994, 57, 1598-1602). None of these, however, have proved a substantial amelioration in terms of both efficacy as well as the prevention of side effects.

Etoposide is a widely used highly effective anti cancer drug against a broad spectrum of tumors including paediatric cancers such as acute lymphatic lymphomas, rhabdomyosarcomas and neuroblastomas as well as in most common adult cancers. It is also used in bone marrow transplantation conditioning regimens. However, the therapeutic use of etoposide is limited by its toxicity involving mainly myelosuppression.

One of the major challenges for successful chemotherapy in cancer in general and high risk leukemia in particular is to overcome multidrug resistance. The majority of patients initially respond to treatment with combinations of various chemotherapeutic agents. However, polychemotherapy may induce multidrug resistant (MDR) cell clones which continue to proliferate in the presence of cytotoxic agents (Dalton W S. Mechanism of drug resistance in hematologic malignancies Semin Hematol. 1997; 34:3-8). The reduction of chemosensitivity in such cell clones would require the administration of cytostatic agents in quantities exceeding the maximum tolerated dose in vivo. One of the best-characterized resistance mechanisms in leukemias and carcinomas is the drug extrusion mediated by p-glycoprotein, the product of the multidrug resistance-1 gene (MDR-1), which has been shown to be associated with poor outcome (Hunault M, Zhou D, Delmer A, et al. Multidrug resistance gene expression in acute myeloid leukemia: major prognosis significance for in vivo drug resistance to induction treatment. Ann Hematol. 1997; 74:65-71; Marie J P, Zhou D C, Gurbuxani S, Legrand O, Zittoun R. MDR1/P-glycoprotein in haematological neoplasms. Eur J Cancer. 1996; 32A:1034-1038.).

A variety of strategies have been developed to avoid or circumvent drug resistance since the introduction of polychemotherapy. Efforts to overcome established drug resistance in patients focus on (i) scheduling, i.e. prolonged low dose therapy such as antifolates in relapsed leukemia or short term high dose administration, e.g. antifolates with subsequent folate-rescue in osteosarcoma, (ii) combination therapy with chemical sensitizers such as MDR-1 inhibitors in the case of MDR-mediated resistance and (iii) combination of chemotherapy with non-chemical sensitizers such as radiotherapy, hyperthermia or hyperbaric oxygen (Dalton W S. Mechanisms of drug resistance in hematologic malignancies. Semin Hematol. 1997; 34:3-8; Joel S P, Slevin M L. Schedule-dependent topoisomerase II-inhibiting drugs. Cancer Chemother Pharmacol. 1994; 34 Suppl:S84-S88; Ishikawa T, Kuo M T, Furuta K, Suzuki M. The human multidrug resistance-associated protein (MRP) gene family: from biological function to drug molecular design. Clin Chem Lab Med. 2000; 38:893-897.)

Only few attempts have been made to directly modify the cytostatic agent in order to find analogues that actively evade drug resistance mechanisms such as a deaminated doxorubicin analogue (Solary E, Ling Y H, Perez-Soler R, Priebe W, Pommier Y. Hydroxyrubicin, a deaminated derivative of doxorubicin, inhibits mammalian DNA topoisomerase II and partially circumvents multidrug resistance. Int J Cancer. 1994; 58:85-94.), and beta-amino derivatives of etoposide (Zhang Y L, Guo X, Cheng Y C, Lee K H. Antitumor agents. 148. Synthesis and biological evaluation of novel 4 beta-amino derivatives of etoposide with better pharmacological profiles. J Med Chem. 1994; 37:446-452; Zhang Y L, Shen Y C, Wang Z Q, et al. Antitumor agents, 130, Novel 4 beta-arylamino derivatives of 3',4'-didemethoxy-3',4'-dioxo-4-deoxypodophyllotoxin as potent inhibitors of human DNA topoisomerase II. J Nat Prod. 1992; 55:1100-1111.). Thus, possible solutions to MDR related failures include the rational design of drugs which are not affected by MDR mechanisms and exhibit reduced systemic toxicity and increased anti-tumor potency.

Resistance against etoposide occurs at distinct cellular levels, involving downregulation of the target enzyme topoisomerase II, downregulation of either pro- or upregulation of anti-apoptotic mechanisms such as bcl-2, and increased metabolism and/or extrusion of the drug from the cell mediated by transport systems. The induction of such transport systems frequently leads to cross resistance against other cytostatic agents, as observed for MDR-1, MRP, or LRP mediated multidrug resistance (Gottesman M M. How cancer cells evade chemotherapy: sixteenth Richard and Hinda Rosenthal Foundation Award Lecture. Cancer Res. 1993; 53:747-754; Borst P, Evers R, Kool M, Wijnholds J. A family of drug transporters: the multidrug resistance-associated proteins. J Natl Cancer Inst. 2000; 92:1295-1302; Borst P, Evers R, Kool M, Wijnholds J. The multidrug resistance protein family. Biochim Biophys Acta. 1999; 1461:347-357.) A major mechanism of drug resistance, documented to occur in hematologic malignancies, is the overexpression of the MDR-1 gene product, P-glycoprotein. Therefore, attempts to overcome transport-system mediated drug resistance focused thus far mainly on modulation of MDR-1 expression (Liu C, Qureshi I A, Ding X, et al. Modulation of multidrug resistance gene (mdr-1) with antisense oligodeoxynucleotides. Clin Sci (Colch ). 1996; 91:93-98.) or coadministration of MDR-1 inhibitors such as cyclosporin (Sonneveld P, Durie B G, Lokhorst H M, et al. Modulation of multidrug-resistant multiple myeloma by cyclosporin. The Leukaemia Group of the EORTC and the HOVON. Lancet. 1992; 340:255-259.), verapamil (Joly P, Lallemand A, Oum'Hamed Z, Trentesaux C, Idoine O, Desplaces A. Effects of verapamil and S9788 on MDR-1 MRNA expression studied by in situ hybridization. Anticancer Res. 1996; 16:3609-3614.) or valspodar (Tai H L. Technology evaluation: Valspodar, Novartis A G. Curr Opin Mol Ther. 2000; 2:459-467.) all of which revealed limited efficacy in vitro and in vivo. These membrane transport proteins extrude a surprisingly wide range of substrates with entirely different structures, possibly due to the fact that common metabolites such as glucuronide, glutathione or sulfate rather than the different drugs are specifically recognized (Zhu B T. A novel hypothesis for the mechanism of action of P-glycoprotein as a multidrug transporter. Mol Carcinog. 1999; 25:1-13.). Therefore, these resistance mechanisms resemble the ubiquitin system, where a plethora of entirely different proteins are "tagged" with ubiquitins in order to be first recognized and then degraded by proteasomes. Thus drug modifications that interfere with molecular "tagging" result in new molecules which may not be cleared from multidrug resistant tumor cells.

Some attempts have been undertaken to synthesise derivatives of etoposide which should allow a more specific targeting of etoposide to the target tissues. EP0423747 reports the synthesis of glycosyl-etoposide-prodrugs which by the action of tumor-specific enzyme conjugates can be cleaved into the effective etoposide drug and a glycosylic residue, whereby, because of the tumor specific enzyme conjugates, the drug is activated only at its preferred site of action. (cf. also U.S. Pat. No. 4,975,278). Shabat et al. (PNAS, vol. 98, 13, 7528-7533) describe the synthesis of an antibody-prodrug system based on etoposide wherein the 4'-phenolic OH-group was masked by an aldol carbamate compound. Such a prodrug alone, however did not show any anti-tumour activity, unless it was combined with a catalytic antibody 38C2, which activates the prodrug to yield etoposide. The prodrugs described in Shabat et al. are only activated by retro-Michael/retro-aldol reactions which do not occur in nature. Only artificial enzymes, like the 38C2. catalytic antibody can catalyse the conversion. The handling and the use of such a prodrug is made more difficult by the additional requirement of the co-application of a catalytic antibody which catalyses the conversion into the active drug. Therefore, none of the above mentioned derivative prodrugs have proven particularly useful in the treatment of the above mentioned cancers.

Prodrugs of various antitumor agents have been synthesised in order to improve their bio-availability, pharmacokinetics and aqueous solubility. WO99/30561 describes a nucleotide-based prodrug wherein the release and activation of the drug component arises from the hydrolysis of the junctional ester bond joining the nucleotide component to the drug component.

U.S. Pat. No. 4,975,278 describes a method for the delivery of cytotoxic drugs to tumor cells by the administration of a tumor-specific antibody-enzyme conjugate that binds to the tumor cells, and the additional administration of a prodrug that is converted at the tumor side, in the presence of the antibody-bound enzyme, to an active cytotoxic drug. This concept has been used in conjunction with etoposide-4'-phosphate or 7-(2'-aminoethyl phosphate)-mitomycin. Again this has been of limited utility so far.

WO94/13324 describes the conversion of drugs into prodrugs by converting their corresponding functional groups into 1-O-alkyl-, 1-O-acyl-, 1-S-acyl- and 1-S-alkyl-sn-glycero-3-phosphate derivatives. None of the reported prodrugs of WO94/13324 have proven particularly effective in the treatment of cancers.

WO98/13059 reports on prodrugs comprising an amino-terminal capped peptide that is a substrate for a peptidohydrolase located on the surface of a metastatic cell. The anticancerdrug typically used for that purpose is doxorubicine, taxol, camptothecin, mitomycin C or esperamycin. The peptidohydrolase that hydrolyses the substrate of the prodrug is typically cathepsin B.

U.S. Pat. No. 5,977,065 describes prodrugs of actinomycine D, doxorubicin, mytomycin C or nitrogen mustard arising from a reaction with 4-nitrobenzylchloroformate.

European Patent Application EP 0320988 to Bristol-Myers Company discloses 4'-esters, 4'-carbonates and 4'-carbamates of 4'-demethylepipodophyllotoxin glucosides for which a certain antitumor activity in animals is reported. The compounds disclosed in EP 0320988 are not capable of overcoming multidrug resistance.

Nicolaou (Nature 1993, 364, 464) and Niethammer et al. (Bioconj. Chem. 2001, 3, 414) report on a paclitaxel prodrug blocked at the C7 hydroxyl group with a dihydroxy propyl sidechain which can be hydrolytically cleaved by a pH-dependent, slow-release mechanism. The resulting prodrug showed some advantages in relation n to the parent drug in that it was more water soluble and could be used at a 3-fold higher maximum tolerated dose (MTD). Paclitaxel is an anticancer agent which is particularly used in breast, lung and ovarian cancers. It is known to promote the irreversible polymerisation of tubulin thereby disrupting the cell devision by cell cycle arrest in the premitotic G2 phase. A second cytotoxic mechanism of paclitaxel is to assist the induction of TNF alpha, an event unrelated to the polymerisation of microtubules. The paclitaxel prodrugs described in the aforementioned publications are unstable in aqueous solution and hydrolyse spontaneously. Therefore the utility of the prodrugs reported in Niethammer et al. is very limited. So far, no prodrug has been reported in relation to etoposide which showed substantially improved efficacy and highly reduced side effects in comparison to the parent molecule. Accordingly it has been an object of the invention to provide for a prodrug of podophyllotoxins which substantially reduces adverse reactions when administered to patient. It has also been an object of the present invention to provide for prodrugs of podophyllotoxins that are stable in aqueous solutions, yet do not require the application of catalytic antibodies for their conversation into the active drug. It has furthermore been an object to provide for prodrugs of podophyllotoxins that allow for a slow release of the drug at the intended side of action, i.e. a tumor. It has also been an object of the present invention to provide for prodrugs of podophyllotoxins that are capable of overcoming multidrug resistance commonly encountered with the parent molecule of the drug. Furthermore it has been an object to provide for a method of preparing such prodrugs as well as a pharmaceutical composition comprising such prodrugs as well as providing potential uses of such prodrugs and such pharmaceutical composition.

This object is solved by a podophyllotoxin represented by formula I

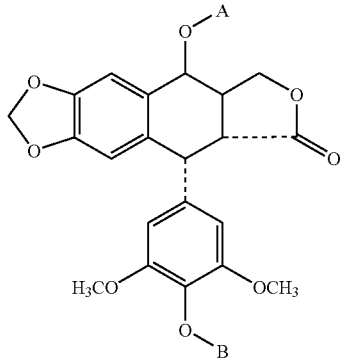

(I)

wherein A is H or is selected from the group comprising carbohydrates, polyols,

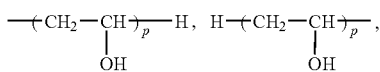

ethylene glycol, propylene glycol, glycerol, penta-, erythritol, polyethyleneglycol and compounds, as represented by formula III below, wherein p is an integer from 2 to 100, and wherein B is represented by formula II —(C=X)—(Y)—(CH$_2$)$_n$-Z (II)

wherein X is selected from the group comprising O, S and NR", Y is selected from the group comprising O, S, and NR", wherein R"=alkyl, aryl or H, n is an integer of from 0 to 6; and Z is a polyhydroxyalkyl group selected from the group comprising ethylene glycol, propylene glycol, glycerol, pentaerythritol, polyethyleneglycol and compounds represented by formula III

(III)

or Z is a polyhydroxyalkyl group, as defined above, which additionally has a dioxolane group attached, or Z is a dioxolane group, or Z is selected from the group comprising targetting moieties for mammalian receptors, antibodies, steroids, transferrin, proteins and peptides having tumor cell associated receptor finding function, In one embodiment, the dioxolane group is selected from the group comprising 2,2-dialkyl-1,3-dioxolane, wherein each alkyl at the 2-position is independently selected from the group comprising unsubstituted and substituted methyl, ethyl, propyl, butyl, pentyl and hexyl.

In one embodiment, Z is a targeting moiety for a mammalian surface membrane receptor or for a mammalian nuclear receptor, or Z is an antibody, steroid, transferrin, protein or peptide having tumor cell associated receptor binding function, wherein, preferably, Z is selected from the group comprising steroids, growth factor receptor inhibiting proteins, peptides and non-peptide mimetics.

In one embodiment, A is selected from the group comprising compounds as represented by formula IV

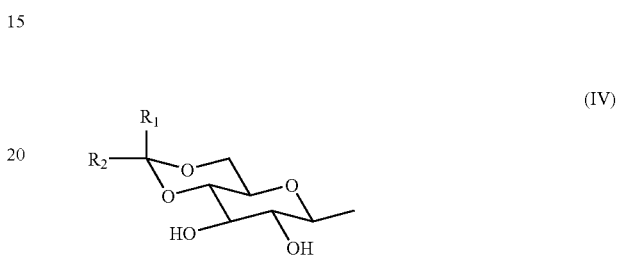

(IV)

wherein $R_1$ and $R_2$ are each $C_1$-$C_{10}$ alkyl; or $R_1$ and $R_2$ and the carbon to which they are attached represent $C_5$-$C_6$ cycloalkyl; or $R_1$ is H and $R_2$ is selected from the group comprising $C_{1-10}$ alkyl, $C_{2-10}$ alkenyl, $C_{3-5}$ cycloalkyl, furyl, thienyl, $C_{6-10}$ aryl, and $C_{7-14}$ aralkyl.

Preferably, $R_1$ is H and $R_2$ is methyl or thienyl.

In one embodiment, X is O and Y is O.

In another embodiment, X is O and Y is S.

In yet another embodiment, X is O and Y is NH.

In a preferred embodiment, the podophyllotoxin is selected from the group comprising

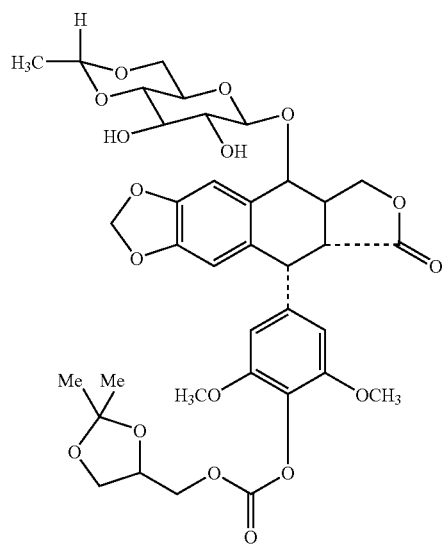

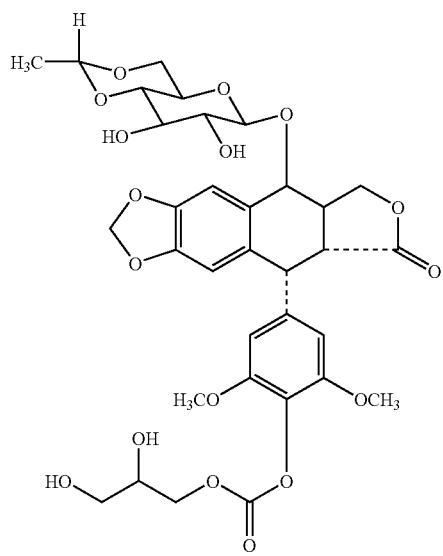
In another embodiment, it is selected from the group comprising
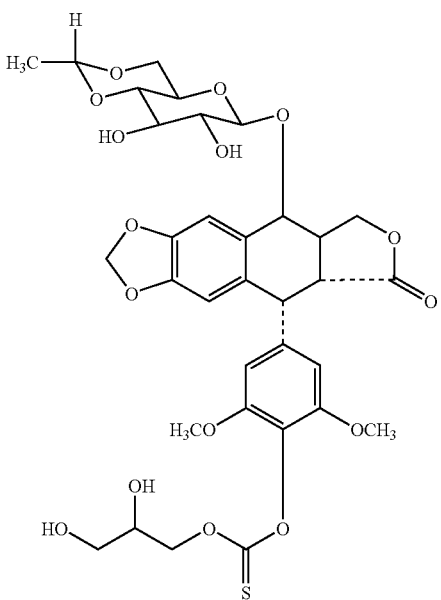
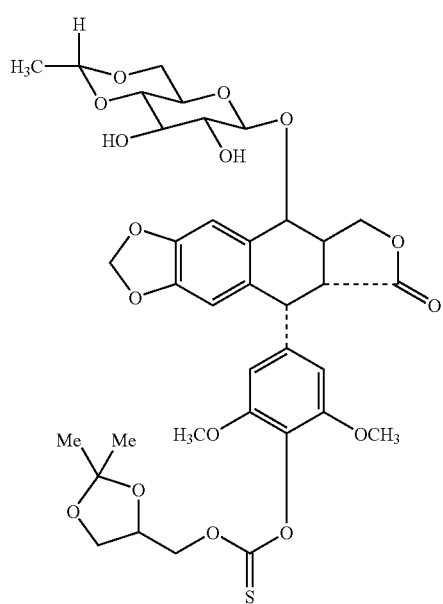
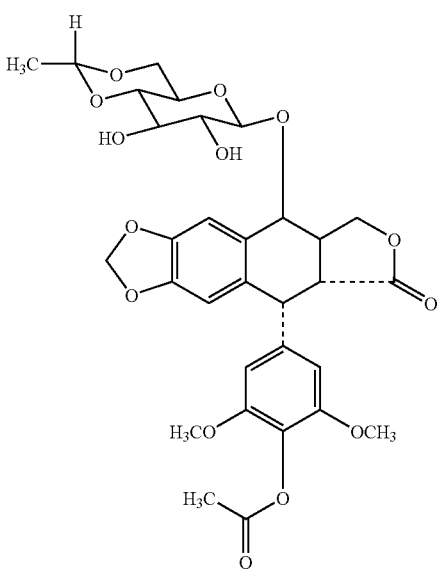

-continued
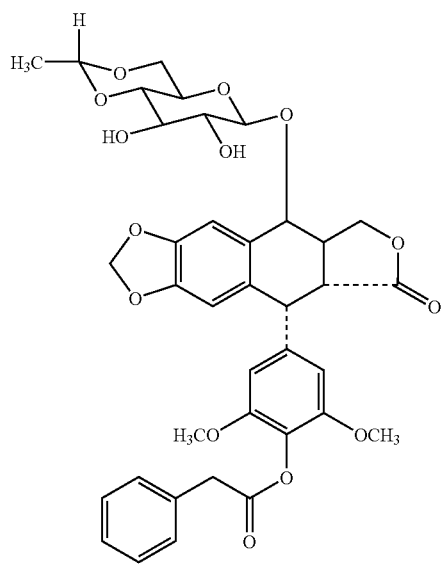
In yet another embodiment, it is selected from the group comprising
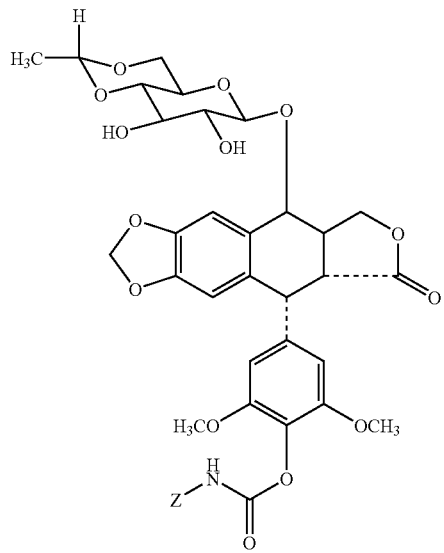
wherein Z is defined as in claim 1, wherein, preferably, the podophyllotoxin is selected from the group comprising
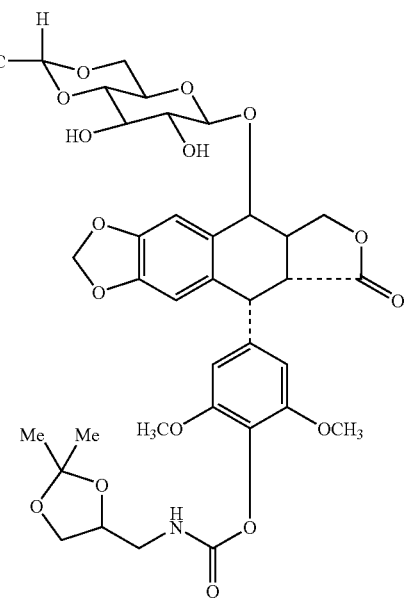
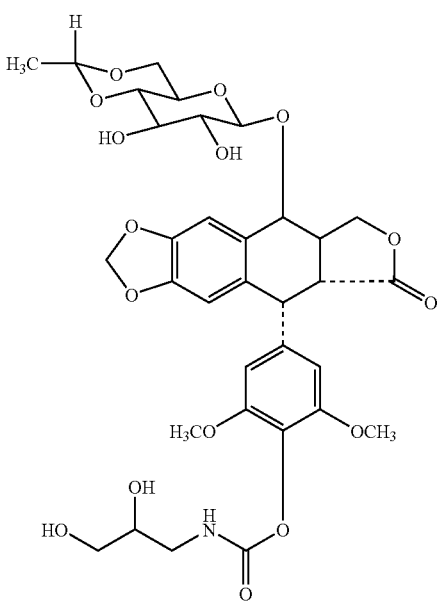

The objects of the present invention are also solved by a method of preparing a podophyllotoxin, characterized in that a compound as represented by formula V

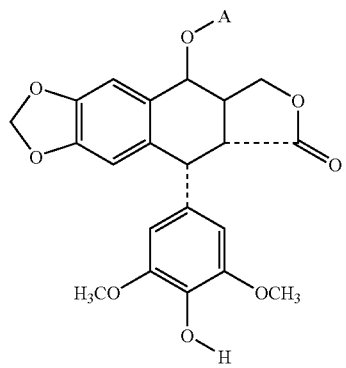

A being as defined before, is reacted with a haloformate W—(C=X)—(Y)—(CH$_2$)$_n$-Z, wherein X, Y, Z and n are as defined before, and W being Cl, F, Br or I, or characterized in that a compound as represented by formula V is reacted with phosgene or trichloromethylchloroformate, to yield a 4'-phenol chloroformate intermediate,
  said 4'-phenol chloroformate intermediate then being reacted with an alcohol or thiol of the formula ZYH, to yield the corresponding carbonate or thiocarbonate, Y=O or S, and Z being as defined before, or
  said 4'-phenol chloroformate intermediate then being reacted with an amine of the formula HNR"Z to yield the corresponding carbamate, R" and Z being as defined before.

Preferably the compound as represented by formula V is reacted with a compound selected from the group comprising p-nitrophenyl soketalcarbonate, soketalchloroformate, and PEG-chloroformate.

In one embodiment of the method according to the present invention, the product resulting from the method as described before, is hydrolyzed.

The objects of the present invention are also solved by a pharmaceutical composition comprising a podophyllotoxin according to the present invention and a pharmaceutically acceptable carrier.

The objects of the present invention are also solved by a use of a podophyllotoxin according to the present invention or of a pharmaceutical composition according to the present invention for the manufacture of a medicament for the treatment of cell proliferative disorders, wherein, preferably, the cell proliferative disorder is in a child, an adolescent or an adult.

In order to create hydrolytically activated prodrugs of etoposide VP-16 as inactive precursor molecules which are activated by hydrolysis, derivatives of the 4' phenolic hydroxy group were synthesised. In previous studies it could be demonstrated that this 4' phenolic hydroxy group is very important for the cytotoxic activity of etoposide since a stable linker fused to that OH group decreased cytotoxicity by >3 logs (Shabat D, Lode H N, Pertl U, et al. In vivo activity in a catalytic antibody-prodrug system: Antibody catalyzed etoposide prodrug activation for selective chemotherapy. Proc Natl Acad Sci U.S.A. 2001; 98:7528-7533.). The prodrugs reported by Shabat, however, were ineffective in conferring cytotoxicity and did not show any anti-tumour activity unless they were combined with the catalytic antibody 38C2 which activates those prodrugs to yield the active drug. The prodrugs reported in Shabat et al. are only activated by retro-Michael-retro-aldol reactions which do not occur in nature, such that catalytic antibody or specifically tailored enzymes have to be added that are capable of catalysing the conversion. In contrast thereto the prodrugs of the present invention are activated by a simple hydrolysis reaction, yet they are stable at a broad range of pH-values under normal physiological conditions.

In contrast to paclictaxel, podophyllotoxins, in particular etoposide, are topoisomerase II inhibitors, with a wide range of applications in human ma lignancies, including solid tumors and leucemias which are distinct from the field of applications of paclitaxel. For example etoposide is employed for the treatment of acute lymphatic leukemia, acute myeloic leukemia, neuroblastoma, and rhabdomyosarcoma. In contrast to the paclictaxel prodrugs that have been reported in the aforementioned publications (in particular Niethammer et al.) the prodrugs of the present invention are much more stable in aqueous solutions under physiological conditions, yet can be easily hydrolysed by appropriate pH changes. Without wishing to be bound by theory it is presently believed that one reason for that unexpected stability is the hydrophobic nature of the "southern" part of the molecule (i.e. at the phenol ring), in combination with the hydrophobic pocket which is formed at the 4' position by the two neighbouring methoxy groups at the 3' and 5' position, respectively.

Therefore, the rational design of hydrolytically activated prodrugs of VP-16 involves the modification of the chemically reactive 4' phenolic hydroxy group which specifically tailors a desired effect. Depending on the nature of the chemical modification, the activation of the prodrug can be defined to occur at a desired pH dependent rate. The prodrugs of the present invention are stable under a wide range of pH values, yet can be activated by an appropriate change of pH, as well as under physiological conditions in the presence of naturally occurring enzymes, such as for example carboxyl esterases. This will be shown in more detail below.

Therefore it was surprisingly found that by rational design, hydrolytically activated prodrugs of etoposide, that retain full anti-tumor activity against multidrug resistant tumor cells in vitro and in vivo, can be produced.

As used herein the term "proteins and peptides having tumor cell associated receptor finding function " is meant to designate any protein or peptide that is capable of binding a receptor that is associated with tumor cells.

"Targeting moieties for mammalian receptors" are groups that are capable of binding to mammalian receptors. "Growth factor receptor inhibiting proteins, peptides and non-peptide mimetics" is meant to designate any protein, peptide or non-peptide small molecule compound that is capable of inhibiting a growth factor receptor by any mechanism, in particular by binding thereto. "Etoposide and teniposide" is meant to designate compounds of the formula

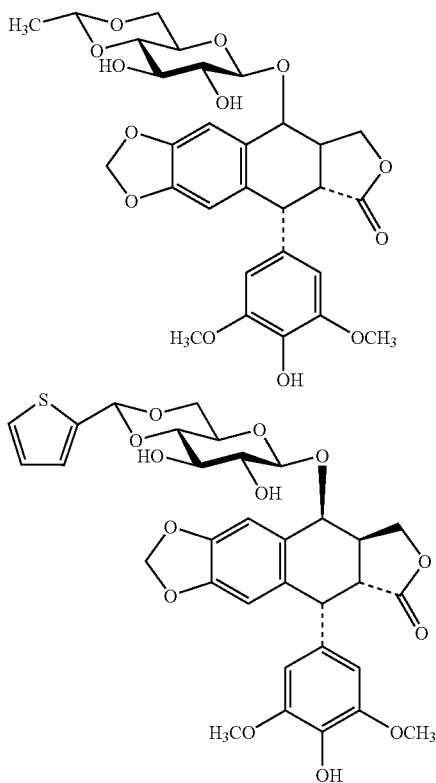

and any protonated form thereof. The term "functionality" is meant to designate any chemical moiety allowing the molecule to which such moiety is attached, to undergo a chemical reaction.

Reference is now made to the figures, wherein

Figure 1:
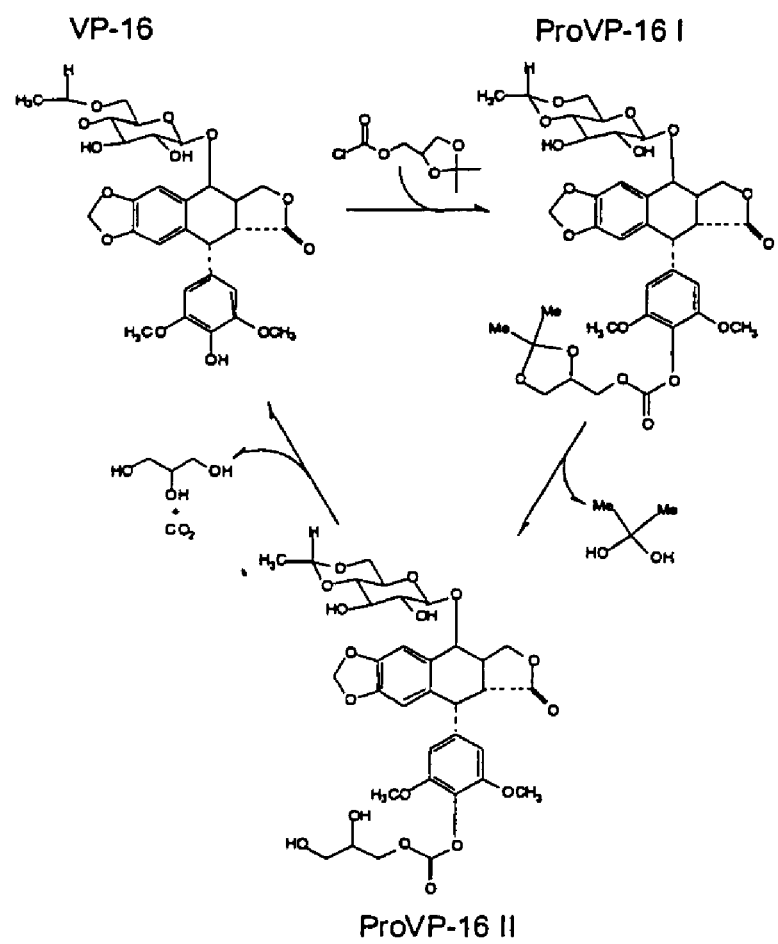
FIG. 1 shows a scheme of synthesis of ProVP-16I and II.

FIG. 1 shows a Scheme of synthesis and activation of ProVP-16 I and II. The synthesis of ProVP-16 I involves the reaction of solketal chloroformate and VP-16 as described in Materials and Methods. Compound ProVP-16 II is synthesized from ProVP-16 I by acid hydrolysis with the elimination of 2,2 dihydroxypropane. The activation of ProVP-16 II to VP-16 occurs with the elimination of glycerol and carbon dioxide.

Figure 2:
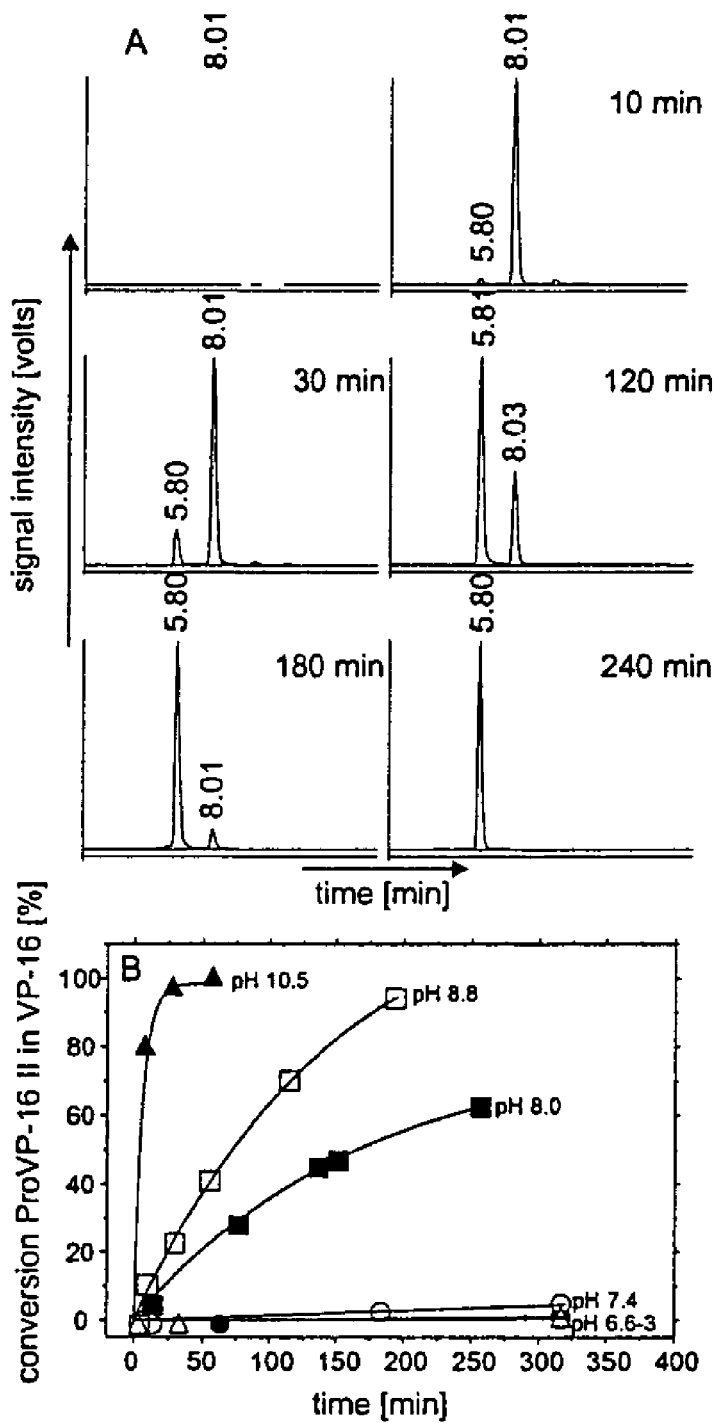
FIG. 2 shows the conversion of ProVP 16I to ProVP-16II and VP-16.

FIG. 2 shows the Conversion of ProVP16 I to ProVP-16 II and VP-16. ProVP-16 I was incubated in THF/2% HCl and samples were periodically analyzed by HPLC at the indicated time points (A). Hydrolytic activation of ProVP-16 II was determined in phosphate buffered saline (PBS) a t the pH levels indicated (B). ProVP-16 I (3 mM) was incubated in PBS solutions and samples were periodically analyzed by HPLC. The percent conversion was calculated from areas under the curve determined by peak integration.

Figure 3:
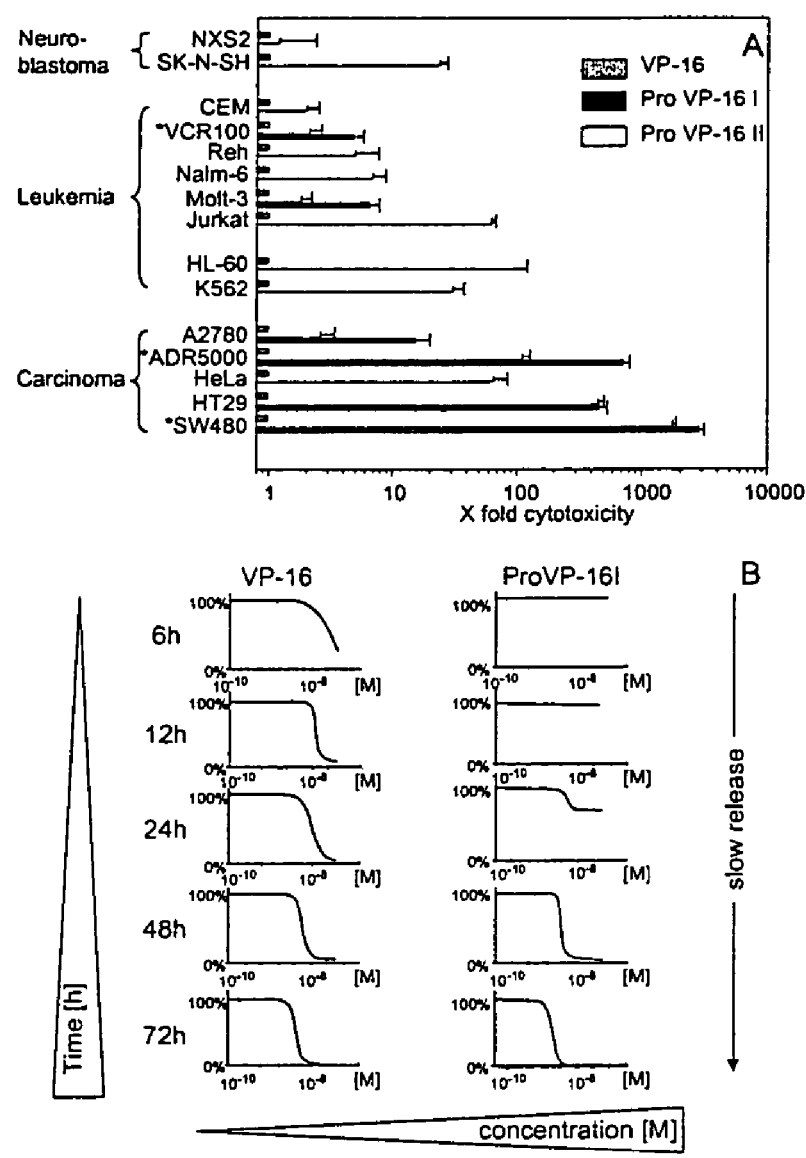
FIG. 3 shows cytotoxicity profiles for ProVP- 16I and II compared to VP-16.

FIG. 3 shows Cytotoxicity profiles for ProVP-16 I and II compared to VP-16. The cytotoxic effect of ProVP-16 I and II was evaluated against a panel of cell lines by triplicate determinations of $IC_{50}$ concentrations for both prodrugs against each cell line (A). The cytotoxicity mediated by the prodrugs relative to VP-16 was calculated according to $IC_{50}$ VP-16÷$IC_{50}$ ProVP-16 I or II. Bars represent mean values ±SD. The differences between ProVP-16 I or II and VP-16 were statistically significant (p<0.01) for all cell lines except NXS2. Stars indicate cell lines with amplified MDR-1 expression.

The slow release kinetics of cytotoxicity by hydrolytically activated ProVP-16 I was determined using Molt-3 cells (B). $10^4$ cells per well were incubated with increasing concentrations ($10^{-10}$ M to $10^{-6}$ M) of ProVP-16 I and VP-16 in 96 well plates. At the time points indicated, cell viability was determined in triplicate by the XTT assay as described in Materials and Methods. Per cent cell viability was calculated from optical density measurements at 450 nm according to OD $450_{sample}$÷OD $450_{untreated}$×100%. Results were plotted as a semilogarithmic function of drug concentration.

Figure 4:
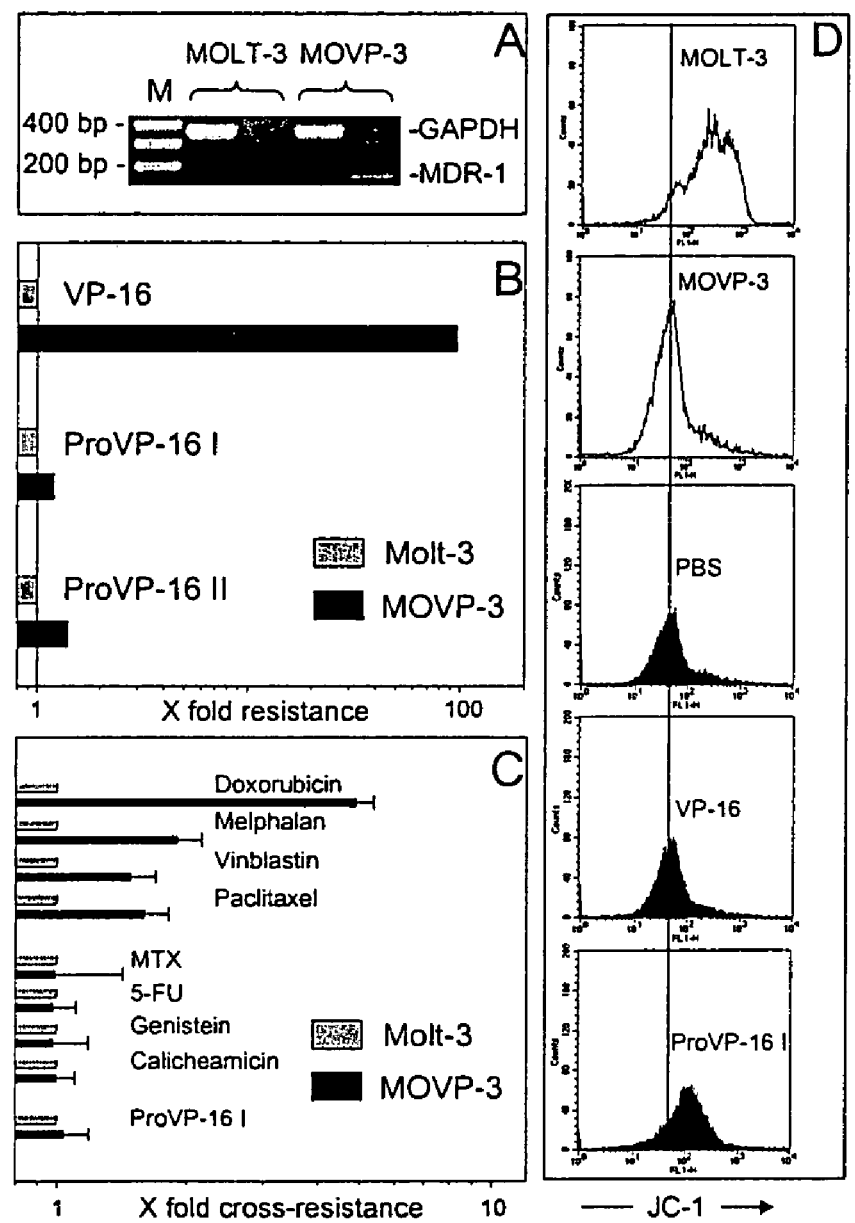
FIG. 4 shows the effect of Pro VP-16I and II on multidrug resistant MOVP-3 cells.

FIG. 4 shows the Effect of ProVP-16 I and I on multidrug resistant MOVP-3 cells. The newly generated VP-16 resistant MOVP-3 cell line was analyzed for MDR- 1 gene expression (A), resistance against VP-16 induced cytotoxicity (B) and cross resistance to MDR-1 drugs which are known substrates for p-glycoprotein (C). MDR-1 gene expression was determined by RT-PCR analysis on total RNA isolated from MOVP-3 and Molt-3 cells, respectively (6A). Expression of GAPDH was used as a control for the integrity of the cDNA. Resistance of MOVP-3 cells against VP-16 was calculated from IC50 concentrations according to IC50 $_{MOVP-3}$÷IC50$_{Molt-3}$(n=3) and results compared to effects observed with ProVP-16 I and II (6B). Differential findings between Molt-3 and MOVP-3 cells obtained with VP-16 were statistically significant (p<0.001) in contrast to ProVP-16 I and II (p>0.05). (6C) Cross-resistance of MOVP-3 cells against MDR-1 drugs (doxorubicin, melphalan, vinblastine and paclitaxel) was calculated from IC50 values (n=3) as described in 6B). Results for non-MDR-1 drugs (MTX, 5-FU, genistein, calicheamicin θ, ProVP-16 I) are shown as controls. Differential findings for MDR-1 drugs between MOVP-3 and Molt-3 cells were all statistically significant (p<0.01) in contrast to non-MDR-1 drugs (p>0.05).

Figure 5:
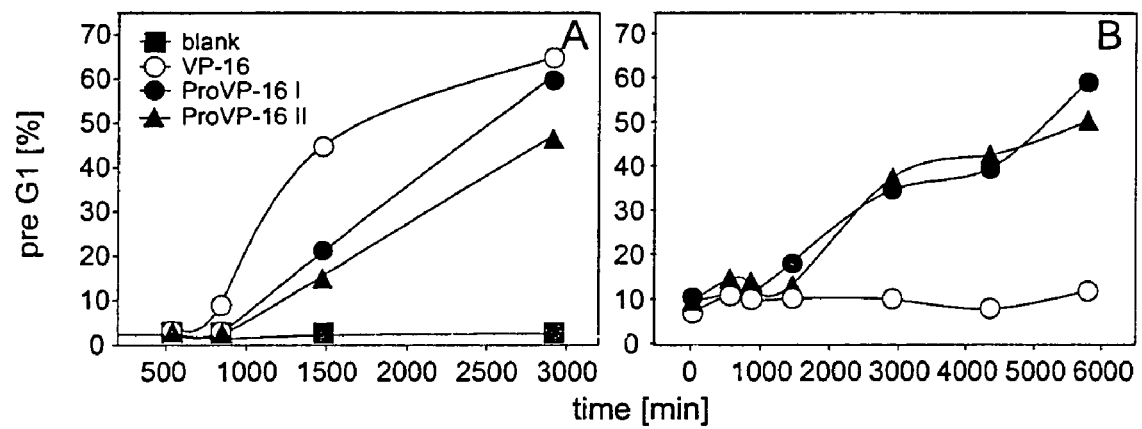
FIG. 5 shows the induction of apoptosis by ProVP-16I and II in resistant cells.

FIG. 5 shows the Induction of apoptosis by ProVP-16 I and II in resistant cells. The effect of ProVP-16 I and II ($5\times10^{-7}$ M) on the cell cycle was analyzed in Molt-3 (A) and MOVP-3 (B) cells and results were compared to VP-16 ($5\times10^7$ M). Cells were harvested at indicated time points (n=3), fixed, stained with propidium iodide and analyzed by FACS as described in Materials and Methods. Per cent cells in pre G1 (apoptosic cells) were calculated from DNA histograms.

Figure 6:
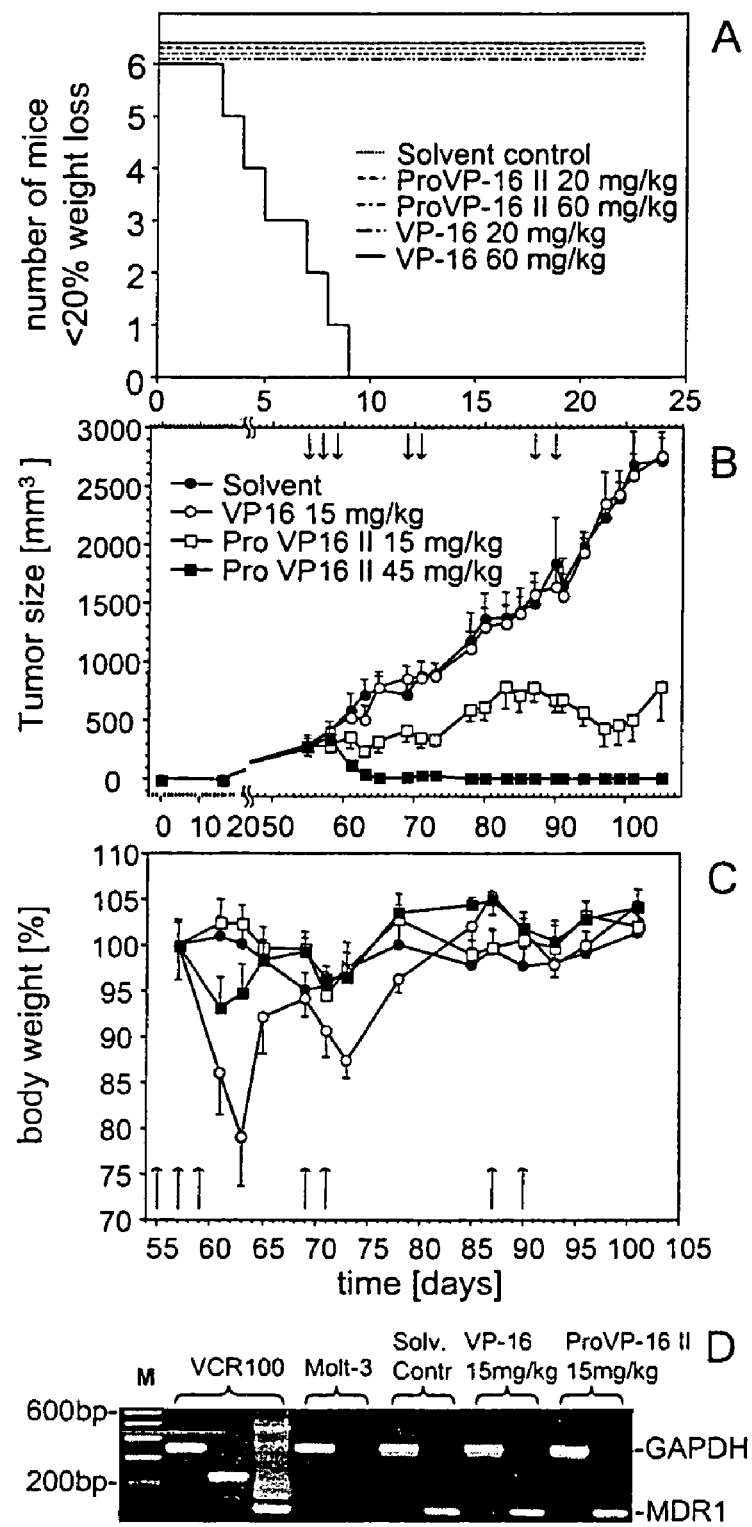
FIG. 6 shows the toxicity and anti-tumour response following ProVP-16II therapy in mice.

FIG. 6 shows the Toxicity and anti-tumor response following ProVP-16 II therapy in mice. A/J mice (n=6) were injected i.p. with ProVP-16 II (20 and 60 mg/kg) and VP-16 (20 mg/kg) on days 1, 3, 5, 7, 9, and 11 and with VP-16 (60 mg/kg) on days 1,3 and 5 (A). The body weight was determined for each animal over time and calculated as per cent of total weight observed on day 0. An event as indicated by Kaplan Maier plots is defined by loss of body weight greater than 20%.

The anti-tumor effect of ProVP-16 II therapy was determined in a multidrug resistant xenograft model (B,C). SCID mice (n=7) were injected s.c. with $5\times10^6$ MOVP-3 cells and primary tumors of 250 mm$^3$ average size were established 55 days after inoculation. Treatment consisted of i.p. injections with Pro VP-16 II (45 and 15 mg/kg), VP-16 (15 mg/kg) and solvent on days 55, 57, 59, 69, 71, 87 and 90 after tumor cell inoculation. Tumor growth was monitored by microcaliper measurements and tumor size was calculated as described in Materials and Methods (B). Differential findings between experimental groups of animals treated with ProVP-16 II (45 and 15 mg/kg) and control groups (solvent and VP-16) were statistically significant ($p<0.001$ after day 63) (B). The body weight of treated animals was determined over time and calculated as per cent of body weight on day 57 (C).

At the end of the treatment experiment, remaining s.c. tumors were removed and analyzed by RT-PCR for- gene expression of MDR-1 except mice treated with 45 mg/kg with no residual tumor. Representative signals of one tumor of each group is depicted and compared to MDR-1 expressing VCR-100 cells used as a positive control. The presence of a 229 or 127 bp signals indicate expression of MDR-1.

The podophyllotoxins according to the present invention have surprisingly proven to be particularly effective in mediating cytotoxicity. Various derivatives of etoposide were synthesized and their activation mechanism via hydrolysis was clearly established (see examples that follow). Importantly, at physiological buffer conditions, the prodrugs remained stable. A prodrug of etoposide with a stable carbamate linker to block the 4' hydroxy group of VP-16 had already been shown to be completely stable under physiological buffer conditions (Shabat D, Lode H N, Pertl U, et al. In vivo activity in a catalytic antibody-prodrug system: Antibody catalyzed etoposide prodrug activation for selective chemotherapy. Proc Natl Acad Sci U S A. 2001; 98:7528-7533.). In contrast to the hydrolytically activated prodrugs of the present invention, exemplified by ProVP-16 I and II, the carbamate prodrug was designed to be activated only by catalysis of a retro-aldol retro-Michael reaction mediated by catalytic antibody 38C2, a reaction which does not occur in nature. It has to be stressed that this carbamate prodrug as opposed to the prodrugs of the present invention was ineffective in mediating cytotoxicity against all tumor cell lines investigated, thus demonstrating a crucial role for the 4' hydroxy group in VP-16 as a biologically relevant center capable of inducing cytotoxicity. The active center is also blocked in the prodrugs described here; however the prodrugs as comprised by the present invention with their hydrolytic activation mechanism do mediate cytotoxicity very effectively. The non-toxic nature of unconverted ProVP-16 I and II is shown by the slow release mechanism demonstrated in Molt-3 cells (FIG. 3) and by the absence of cytotoxic effects for the prodrugs up to 12 h of incubation is in contrast to VP-16. A steady increase of cytotoxic activity of both VP-16 derivatives over time clearly demonstrated that the novel compounds of the present invention are initially stable and non-toxic, but then become activated inside the target cells. The slow release mechanism observed in vitro also accounts for the dramatically decreased systemic toxicity in mice, as demonstrated for ProVP-16 II being tolerated a greater than 3 fold increase in the maximum tolerated dose over the parental compound (FIG. 6).

Further characterization of the prodrugs according to the present invention revealed a higher potency in a number of cancer cell lines compared to VP-16. Thus, in cells with amplified MDR-1 gene expression (VCR 100, ADR 5000 and SW480) more than 3 log greater efficacy of the prodrugs according to the present invention was observed (FIG. 4). This is an increase rarely achieved by MDR-1 modulators (Dalton W S. Mechanisms of drug resistance in hematologic malignancies. Semin Hematol. 1997; 34:3-8; Sonneveld P, Durie B G, Lokhorst H M, et al. Modulation of multidrug-resistant multiple myeloma by cyclosporin. The Leukaemia Group of the EORTC and the HOVON. Lancet. 1992; 340: 255-259; Joly P, Lallemand A, Oum'Hamed Z, Trentesaux C, Idoine O, Desplaces A. Effects of verapamil and S9788 on MDR-1 mRNA expression studied by in situ hybridization. Anticancer Res. 1996; 16:3609-3614; Tai H L. Technology evaluation: Valspodar, Novartis A G. Curr Opin Mol Ther. 2000; 2:459-467; Kang Y, Perry R R. Effect of alpha-interferon on P-glycoprotein expression and function and on verapamil modulation of doxorubicin resistance. Cancer Res. 1994; 54:2952-2958; Hofmann J, Gekeler V, Ise W, et al. Mechanism of action of dexniguldipine-HCl (B8509-035), a new potent modulator of multidrug resistance. Biochem Pharmacol. 1995; 49:603-609.).

Furthermore, functional assays demonstrate that the prodrugs according to the present invention inhibit MDR-1 mediated substrate efflux. Consequently, it appears that the new prodrugs inhibit MDR-1 p-glycoprotein function accounting for the excellent activity against MDR-1 expressing cancer cell lines. Importantly, this dramatic in vitro effect also translated into a long lasting regression of established primary tumors in a drug resistant T-cell leukemia xenograft model in vivo (FIG. 6). In this model, MDR-1 gene expression is stably amplified with a 100× resistance against VP-16 in vitro (FIG. 4) resulting in the complete absence of a therapeutic effect by VP-16 at the maximum tolerated dose (FIG. 6). Interestingly, in such a challenging model exhibiting an artificially high drug resistance, treatment with the prodrugs according to the present invention can induce a dramatic anti-tumor response (FIG. 6). This is of particular importance since such a high MDR-1 amplification is rarely observed in patients following poly-chemotherapy even in relapsed malignancies (Beck J, Handgretinger R, Dopfer R, Klingebiel T, Niethammer D, Gekeler V. Expression of mdr1, mrp, topoisomerase II alpha/beta, and cyclin A in primary or relapsed states of acute lymphoblastic leukaemias. Br J Haematol. 1995; 89:356-363; Beck J F, Bohnet B, Brugger D, et al. Expression analysis of protein kinase C isozymes and multidrug resistance associated genes in ovarian cancer cells. Anticancer Res. 1998; 18:701-705.).

An important finding of this study is the highly effective anti-tumor response observed in multidrug resistant models with the prodrugs of the present invention in vitro and in vivo, suggesting that therapy with them will lead to a significant improvement over existing chemotherapy with ordinary podophyllotoxins.

The examples that follow are merely intended to illustrate, not to limit the scope of the present invention.

EXAMPLE 1

Materials: 2,3-bis(2-methoxy-4-nitro-5-sulfophenyl)-5-[(phenylamino)carbonyl]-2H-tetrazolium hydroxide (XTT), VP-16, solketal, organic solvents and phenazine methosulfate (PMS) were obtained from Sigma-Aldrich (Deisenhofen, Germany). Cell culture reagents, restriction enzymes and other molecular biology reagents were from Life Technologies (Karlsruhe, Germany).

Cells: Tumor cell lines were grown in RPMI, 10% FCS (Nalm-6, Reh, Molt-3, Jurkat, HL-60, K562, HeLa, CEM, A2780, SW480) or DMEM, 10% FCS (NXS2, SK-N-SH, HT-29) in the presence of 100 IU/ml penicillin/streptomycin (P/S) and propagated under standard tissue culture conditions (5% $CO_2$, 37° C.). All cell lines were obtained from ATCC, Rockville, Md. except NXS2 which was previously described (Lode H N, Xiang R, Varki N M, Dolman C S, Gillies S D, Reisfeld R A. Targeted interleukin-2 therapy for spontaneous neuroblastoma metastases to bone marrow. Journal of the National Cancer Institute. 1997; 89:1586-1594.) and VCR100, ADR5000 and A2780 which were kindly provided by James Beck, Greifswald, Germany (Beck J, Handgretinger R, Dopfer R, Klingebiel T, Niethammer D, Gekeler V. Expression of mdrl, mrp, topoisomerase II alpha/beta, and cyclin A in primary or relapsed states of acute lymphoblastic leukaemias. Br J Haematol. 1995; 89:356-363; Beck J F, Bohnet B, Brugger D, et al. Expression analysis of protein kinase C isozymes and multidrug resistance associated genes in ovarian cancer cells. Anticancer Res. 1998; 18:701-705.). Molt-3 cells were used to generate an etoposide resistant subline MOVP-3 by continuous exposure to increasing amounts of VP-16. After a time period of 6 months, MOVP-3 cells were stable and propagated in the presence of 1 µM VP-16 and used for further in vitro and in vivo experiments.

Mice: Female A/J mice and FOX CHASE™ C.B-17/lcr-Crl-scid BR mice were obtained at 8 weeks of age from Charles River Laboratories, Sulzfeld, Germany. They were housed in the pathogen-free mouse colony at our institution in groups of 8 mice. Mice were fed ad libitum on standard mouse laboratory chow. Animal experiments were performed according to the German guide for the care and use of laboratory animals, i.e. "Tierschutzgesetz".

Analytical chemistry of proetoposides: The synthesis of proetoposides and analysis by HPLC has been previously reported Wrasidlo W, Schroeder U, Bernt K, et al. Synthesis, hydrolytic activation and cytotoxicity of etoposide prodrugs. Bioorg Med Chem Lett. 2002; 12. 557-560, which is hereby incorporated by reference in its entirety.

RNA isolation, reverse transcription and PCR amplification: Isolation of total cellular RNA, cDNA synthesis and RT-PCR-conditions were previously described (Lode H N, Xiang R, Varki N M, Dolman C S, Gillies S D, Reisfeld R A. Targeted interleukin-2 therapy for spontaneous neuroblastoma metastases to bone marrow. Journal of the National Cancer Institute. 1997; 89:1586-1594.). The amplification of human MDR-1 was done with sense 5' GGA GAG ATC CTC ACC AAG CG 3' and antisense 5' GTT GCC AAC CAT AGA TGA AGG 3' for 35 cycles (15 s 96° C., 30 s 60° C., 90 s 72° C.) leading to a 229 bp fragment designated MDR-1. High sensitivity detection was achieved by nested amplification of 1.0 µl MDR-1 after 21 cycles using sense 5' GCT CAG ACA GGA TGT GAG TT 3' and antisense 5' CTG GGT AAT TAC AGC AAG CC 3' for 30 cycles to create a 127 bp fragment. The cDNA integrity was tested by amplification of glycerol-aldehyde-phosphate-dehydrogenase (GAPDH) with sense 5' CGG GAA GCT TGT GAT CAA TGG 3' and antisense 5' GGC AGT GAT GGC ATG GAC TG 3' for 25 cycles leading to a 358 bp fragment. The specificity of all fragments was verified by sequencing.

Functional JC-1 assay: For staining, cells were washed twice and resuspended in PBS containing JC-1 monomer, as previously described (Legrand O, Perrot J Y, Simonin G, Baudard M, Marie J P. JC-1: a very sensitive fluorescent probe to test Pgp activity in adult acute myeloid leukemia. Blood. 2001; 97:502-508.). Briefly, 0.1 µM JC-1 monomer was incubated at 37° C. for 15 minutes with $5\times10^5$ cells/ml and incubated in the presence and absence of etoposide and Pro-VP-16 I and II. Samples incubated with 2 µM cyclosporin A were used as positive controls (data not shown). Cell fluorescence was recorded using a FAC Sort flow cytometer (Becton Dickinson) and JC-1 signals were detected on the FL1-channel (530 nm filter) for analysis of the dye monomer.

Stable transfection of MDR-1: The MDR-1 cDNA was kindly provided in a pUC based plasmid by C. Baum, University of Hamburg. For mammalian expression, the MDR-1 cDNA was cloned into the bicistronic eukaryotic expression plasmid pIRESpuro using NotI and BamHI restriction sites. pMDR-IRESpuro was transfected into Molt-3 cells by electroporation (960 µF, 250V). Stable transfectants were selected with 300 ng/ml puromycin. MDR-1 expression was determined by FAC S-analysis (FAC S-calibur, Becton Dickinson, Bedford, Mass.) using 1 µg/ml MDR- I specific mAb (C. Baum, University of Hamburg).

Cytotoxicity assay: Cytotoxicity was determined by the XTT tetrazolium/formazan assay as previously described (Scudiero D A, Shoemaker R H, Paull K D, et al. Evaluation of a soluble tetrazolium/formazan assay for cell growth and drug sensitivity in culture using human and other tumor cell lines. Cancer Res. 1988; 48:4827-4833.). Briefly, cells were seeded in 96 flat bottom well plates at a density of $10^4$/well in 100 µl media and exposed to drug concentrations ranging from $10^{-4}$ to $10^{-12}$ M. At the indicated time points (6-72 hr), cell viability was assessed by adding 50 µl XTT-reagent (1 mg/ml in serum free RPMI) activated with 0.2% v/v PMS (1.53 mg/ml in PBS) incubated at 37° C. for 4 h. Plates were analyzed in a Thermomax (Molecular Devices) micro plate reader at 450 nm. OD values were plotted as a function of drug concentration and the curves were integrated using the softmax software to obtain the $IC_{50}$ concentration values.

Cell cycle analysis: Distinct phases of the cell cycle were determined in a standard assay using propidium iodide. Briefly, cells were seeded in 24 well plates ($10^5$/well) and incubated with VP-16 or ProVP-16 I and II. At indicated time points, cells were harvested and fixed in 4.5 ml ethanol (75%, −20° C.) for at least 12 h (4° C.). Cells were washed in PBS (pH 7.4) and resuspended in 250 µl PBS containing RNAse (0.3 mg/ml) and propidium iodide (50 µg/ml) and incubated in the dark (30 min, RT). The DNA histograms defining distinct phases of the cell cycle were subsequently determined in duplicates by FACS analysis and average results were expressed as per cent.

Toxicity studies in mice: Stock solutions of 10 mM etoposide and proetoposide were prepared in 50:50 v/v cremophor: ethanol, and diluted to the final concentration in PBS (pH 7.4). A/J mice, 8 to 10 weeks of age were injected i.p. with 20 mg/kg or 60 mg/kg of either etoposide or proetoposide, or with solvent control (25% DMSO, 12.5% ethanol, 12.5% cremophor, 50% PBS), on day 1, 3, 5, 7, 9, and 11. VP-16 (60 mg/kg) was only injected on days 1,3 and 5. Body weights and survival were monitored over time.

Anti-tumor effect in a T-cell leukemia xenograft model: Primary tumors were induced by injection of $5\times10^6$ MOVP 3 cells in 100 µl PBS (pH 7.4) into the skin of the left lateral flank of each SCID mouse. Established primary tumors were palpable 55 days after injection. Mice (n=8) were treated by intraperitoneal injection of solvent (25% DMSO, 12.5% ethanol, 12.5% cremophor, 50% PBS), VP-16 (15 mg/kg) and Pro VP-16 II (15 and 45 mg/kg) in a total volume of 200 µl. Each mouse received a total of 7 injections on days 55,57,59,69, 71,87,90 after tumor cell inoculation. Primary tumor size was determined over time by micro caliper measurements and volumes were calculated according to $\frac{1}{2}\times\text{with}^2\times\text{length}$. Body weight was determined on a standard digital scale.

Statistics: The statistical significance of differential findings between experimental groups of animals was determined by two-tailed Student's t test. Findings were regarded as significant if two-tailed p values were <0.01.

Chemistry of etoposide prodrug activation: In order to establish that ProVP16-I and II are indeed prodrugs, we first determined their activation characteristics in vitro by HPLC (FIG. 1,2). Conversion of ProVP-16 I into ProVP-16 II and subsequent release of VP-16 follows a two step activation mechanism (FIG. 1). First, ProVP-16 I converts to ProVP-16 II with the elimination of 2,2-dihydroxypropane within 2 h with some degradation (about 10%) of the glycoside moiety under -acid conditions (THF, 2N HCL) (FIG. 2A). Second, ProVP-16 II hydrolyses into VP-16 under basic pH conditions with the elimination of glycerine (FIG. 1,2B). In all experiments, conversion-time curves exhibited first order kinetics. Importantly, under physiological buffer conditions (PBS, pH 7.4, 37° C.), ProVP-16 II is stable with a conversion rate of <5% in 5 up to 18 h. ProVP-16 I is completely stable with no measurable conversion in PBS (pH 7.4, 37° C.) and in contrast to ProVP-16 II, it is inert also under basic buffer conditions (pH <10.0). This unusual hydrolytic stability of ProVP-16 I is attributed to the hydrophobic nature of the entire southern region of this molecule and, to a lesser extent, also to steric hindrance from the two ortho methoxy groups surrounding the carbonate moiety.

The utility of the prodrugs according to the present invention is also evident from the fact that they are activated, i.e. hydrolysed in the presence of naturally occurring enzymes, but show stability in aqueous solutions over a wide range of pH-values.

Activation of ProPV-16 I and II occurs in the presence of serum with conversion half lifes of 750.8 min and 56.1 min, respectively. Porcine liver caboxyl esterase also mediated conversion of ProVP16 I and II into VP-16 with conversion half lifes of 14.2 min and 514.1 min, respectively. These findings clearly indicate enzymatic prodrug activation at pH 7.4 by carboxyl esterases (Table 1).

TABLE 1

Kinetic parameters for hydrolysis of etoposide prodrugs

| compound | media (37° C. ± 0.5) | PH (±0.1) | $k_{obs}$ ($10^{-3}$-$min^{-1}$)[a] | $t_{1/2}$ (min) |
|---|---|---|---|---|
| Prodrug I 2 | PBS buffer | 5.0-10.0 | no conversion | — |
|  |  | 11.8 | 8.333 ± 0.50 | 83.16 |
|  | human serum | 7.3 | 0.923 ± 0.046 | 750.8 |
|  | esterase[b] | 7.3 | 48.89 ± 3.62 | 14.17 |
| Prodrug II 3 | PBS buffer | 5.0-7.3 | no conversion | — |
|  |  | 8.0 | 3.201 ± 0.428 | 216.49 |
|  |  | 8.8 | 7.142 ± 0.351 | 97.03 |
|  |  | 10.5 | 100.01 ± 12.72 | 6.93 |
|  | human serum | 7.3 | 12.36 ± 0.965 | 56.07 |
|  | esterase | 7.3 | 1.348 ± 0.081 | 514.10 |

[a]mean ± SD
[b]porcine liver carboxyl ester hydrolase

EXAMPLE 2

Activity of ProVP-16 I and II against leukemia and cancer cell lines: The cytotoxicity of these two proetoposides was tested against a panel of tumor cell lines using the XTT vital stain antiproliferation assay (FIG. 3A). For the majority of human tumor cell lines tested both proetoposides were substantially more active than the parent compound with $IC_{50}$ values 1000 fold lower with SW480 colon carcinoma, 100-1000 fold lower with HT-29 colon carcinoma, ADR5000 ovarian carcinoma and HL-60 pre B-cell leukemia, 10-100 fold lower with HeLa cervical carcinoma, A2780 ovarian carcinoma, K562 chronic myeloid leukemia, Jurkat T-cell leukemia, and SK-N-SH neuroblastoma, and 2-10 fold lower with Molt-3 T-cell leukemia, Reh and Nalm-6 pre B-cell leukemia, VCR100 T-lymphoblastic leukemia and CEM T-lymphoblastic leukemia cells. Only three cell lines, NXS2 murine neuroblastoma (FIG. 3A), CHO Chinese hamster ovary, and Hamms human colon carcinoma cells responded equally well to etoposide and proetoposides. Two cell lines, the doxorubicin-resistant ADR5000 and the vincristine-resistant VCR100, both with amplified MDR-1 expression, revealed a higher cytotoxic potential for both proetoposides than for the non-resistant parental cell lines A2780 and CEM.

The time course of cytotoxic action of Pro-VP16 I was followed by using Molt-3 T-cell leukemia cells (FIG. 3B). The results indicate a delayed onset of cytotoxic activity by ProVP-16 I, starting after 24 hr of incubation. At that time point, the cytotoxic effect of parental VP-16 was already almost completely established. The cytotoxic effect of ProVP16 I was completed 48-72 h after incubation ($IC_{50}$ $1.0 \times 10^{-8}$) and exceeded that of VP-16 ($IC_{50}$ $6.5 \times 10^{-8}$ M). Similar results were observed with ProVP-16 II (data not shown). These findings indicate a slow release mechanism of cytotoxic activity from ProVP-16 I and II which is absolutely consistent with the prodrug concept.

EXAMPLE 3

Effect of ProVP-16 I and II on multidrug resistant cells: Based on the finding that ProVP-16 I and II are also more effective than VP-16 in natural MDR-expressing cell lines (FIG. 3), the question was addressed whether these prodrugs could overcome artificial MDR in vitro. For this purpose, the MDR-1 negative cell line Molt-3 was used to generate a resistant subclone MOVP-3 (FIG. 4A). MDR-1 mRNA expression in MOVP-3 cells was determined by RT-PCR (FIG. 4A) while increased MDR-1 protein expression on the cell surface was established by FACS-analysis using UIC2 monoclonal antibody. Extended gene expression analyses also looking at MRP, LRP, Topisomerases I, IIα and IIβ as well as Bax and Bcl-2 (data not shown) reveal that the only difference accounting for drug resistance in MOVP-3 cells in contrast to Molt-3 is expression of MDR-1. This was further confirmed by functional characterization of the subline revealed a 100-fold resistance against etoposide with $IC_{50}$ values of $2 \times 10^{-6}$ M for MOVP-3 and $2 \times 10^{-8}$ M for Molt-3 cells (FIG. 4B). However, MOVP-3 cells remained almost fully sensitive towards ProVP16 I and II with no significant difference in proetoposide mediated cytotoxicity between parental Molt-3 and drug resistant MOVP-3 cells, with $IC_{50}$ values of $2 \times 10^{-8}$ M for both prodrugs and cell lines. Similar results were obtained in Molt-3 cells following stable transfection with MDR-1 cDNA using pMDR-IRESpuro (Molt-3/MDR-1) that resulted in resistance against etoposide, doxorubicin, taxol and vinblastine (data not shown). Molt-3/MDR-l cells also remained fully sensitive against ProVP-16 I and II. Controls stably transfected with empty vector (pIRE-Spuro) or a vector containing GFP revealed no resistance to any of the drugs tested.

Furthermore the type of resistance in the MOVP-3 subline used was characterised by assessing the extent of cross resistance. MOVP-3 cells displayed cross resistance against all MDR-1 type drugs (etoposide, doxorubicin, paclitaxel, vinblastine) in contrast to non-MDR-1 drugs (MTX, 5-FU, Genistein, Calicheamicin θ) (FIG. 4C). In summary, these findings clearly demonstrate that ProVP-16 I and II can overcome MDR- 1 mediated multidrug resistance in vitro.

In a functional MDR-1 assay using JC-1 dye, an increased JC-1 efflux in MOVP-3 cells could be demonstrated in contrast to Molt-3 controls as indicated by a decrease in the FL-1 signal in the resistant subline in contranst to Molt-3 parental cells (FIG. 4D). This decrease was abrogated by coincubation with $3 \times 10^{-4}$ M Pro-VP-16 I (FIG. 4D) and inhibited MDR-1 mediated efflux over a broad concentration range down to $10 \times 10^{-6}$ M (data not shown). Interestingly, VP-16 used at equimolar concentrations was ineffective in modulating MDR-1 function as indicated by a JC-1 signal not different from PBS controls. These findings clearly indicate that the prodrug design directly decreases MDR-1 mediated substrate efflux.

In order to evaluate the cytotoxic mechanism mediated by ProVP-16 I and II in multidrug resistant MOVP-3 cells, the effect of these drugs on the cell cycle was analyzed at concentrations ranging from 10 μM to 1 μM and compared to Molt-3 parental cells. Typical results obtained with 0.5 μM prodrugs are shown in FIG. 5. Specifically, asynchronous MOVP-3 (FIG. 5 B) and Molt-3 (5 A) cells were incubated with VP-16, ProVP-16 I and II for 72 h. Periodically cells were subjected to cell cycle analysis at indicated time points. Results clearly indicate that both, ProVP-16 I and II at 0.5 μM (FIG. 5B) as well as for the entire concentration range (10 nM-1 μM) (data not shown) are very effective in inducing a steady increase in the pre-G1 peak in MOVP-3 cells after 24 h, characteristic of apoptosis. In contrast to the prodrugs, VP-16 was ineffective to induce apoptosis, consistent with elimination of VP-16, but not ProVP-16 I and II, by MDR-1. Induction of apoptosis was also demonstrated in Molt-3 parental cells over the entire concentration range (0.5 μM, FIG. 5A). VP-16 was demonstrated to induce apoptosis in Molt-3 cells to a similar extent as ProVP-16 I and II. Overall, these results suggest that ProVP-16 I and II are no substrates for MDR-1.

EXAMPLE 4

In vivo toxicity and efficacy of ProVP-16 II in a multidrug resistant T-cell leukemia xenograft model: Based on the in vitro findings that revealed no differences between ProVP-16 I and II, ProVP-16 II was selected for in vivo experiments because of higher water solubility. First, systemic toxicity of ProVP-16 II was determined in A/J mice (n=6) injected i.p. with VP-16 and ProVP-16 II (FIG. 6A). All mice receiving 20 mg/kg VP-16 survived with an average weight loss of 10%. In contrast, 5/6 mice treated with 60 mg/kg VP 16 showed a weight loss >20%. These findings sharply contrast with the results obtained with ProVP-16 II. In that case administration of 20 and 60 mg/kg ProVP-16 II was well tolerated with no death in either experimental group. Only mice receiving 60 mg/kg ProVP-16 II revealed a transient weight loss of <10 % in contrast to 20 mg/kg ProVP-16 II, which maintained stable average body weights. Thus, the maximum tolerated dose defined by a decrease in body weight <20% was established at 20 mg/kg for VP-16 and at 60 mg/kg for ProVP-16 II, consistent with a decrease of systemic toxicity of by the prodrug design by at least a factor 3.

Second, the anti tumor effect of ProVP-16 II was determined in a multidrug resistant xenograft model of T-cell leukemia and compared to VP-16. Established primary tumors were induced by s.c. injection of 5×10$^6$ multidrug resistant MOVP-3 cells and tumor growth was followed over a time period of 105 days. Treatment was initiated 55 days after tumor cell inoculation by i.p. injection at an average tumor size of 250 mm$^3$. The dose levels for VP-16 (15 mg/kg) and ProVP-16 II (15 and 45 mg/kg) were selected based on results shown in FIG. 6A to further reduce systemic toxicity. Treatment with 45 mg/kg ProVP-16 II induced a regression of established primary tumors in 7/7 animals 10 days after initiation of treatment, which was stable for over 2 months (FIG. 6B). This treatment was well tolerated with a transient weight loss of only 6% (FIG. 6C). This finding was in contrast to that observed in mice treated with 15 mg/kg VP-16, which showed no anti-tumor response and revealed continuous primary tumor growth identical to control mice treated only with solvent. However, significant toxicity was observed in mice treated with 15 mg/kg VP-16 who exhibited a transient average weight loss of 20% (FIG. 6C). In fact, mice receiving 15 mg/kg ProVP-16 II showed no measurable weight loss (FIG. 6C) and presented with a dramatic reduction in primary tumor growth in contrast to mice treated with the equivalent amount of 15 mg/kg VP-16. In order to determine whether MDR-1 expression remained stable over the course of the experiment, RNA was isolated from tumor explants at day 105 and all tumors investigated revealed an MDR-1 signal by RT-PCR (FIG. 6D).

The features of the present invention disclosed in the specification, the claims and/or in the accompanying drawings may, both separately and in any combination thereof, be material for realising the invention in various forms thereof.

The invention claimed is:

1. A podophyllotoxin it which is selected from the group consisting of

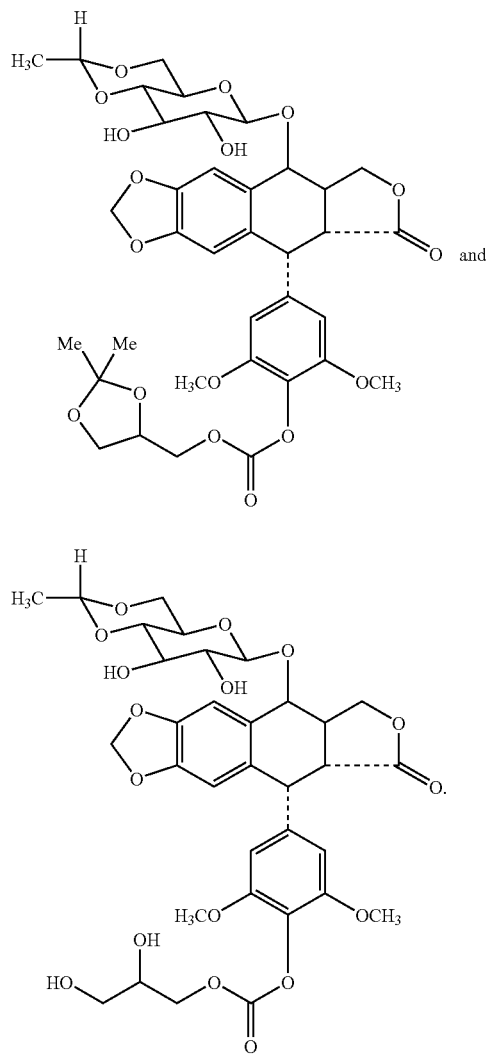

2. A podophyllotoxin represented by the formula:
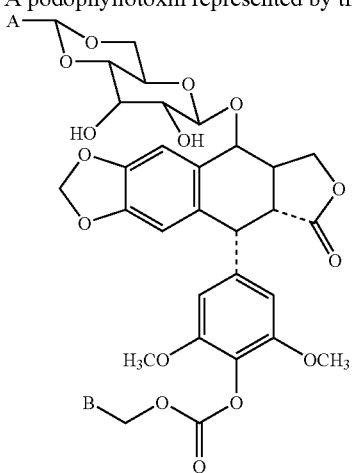
wherein A is —CH$_3$ or  ; and
wherein B is 
![B structure 1] or ![B structure 2]
* * * * *

UNITED STATES PATENT AND TRADEMARK OFFICE
CERTIFICATE OF CORRECTION

| | | |
|---|---|---|
| PATENT NO. | : 7,582,778 B2 | Page 1 of 1 |
| APPLICATION NO. | : 10/497521 | |
| DATED | : September 1, 2009 | |
| INVENTOR(S) | : Gaedicke et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (578) days Delete the phrase "by 578 days" and insert -- by 1,215 days --

Signed and Sealed this

Thirty-first Day of August, 2010

David J. Kappos
*Director of the United States Patent and Trademark Office*